(12) United States Patent
Kim et al.

(10) Patent No.: US 9,670,469 B2
(45) Date of Patent: Jun. 6, 2017

(54) UDP-GLYCOSYLTRANSFERASE DERIVED FROM GINSENG AND USE THEREOF

(71) Applicants: KOREA ADVANCED INSTITUTE OF SCIENCE AND TECHNOLOGY, Daejeon (KR); INTELLIGENT SYNTHETIC BIOLOGY CENTER, Daejeon (KR)

(72) Inventors: Sun-Chang Kim, Daejeon (KR); Gil Tsu Choi, Daejeon (KR); Suk Chae Jung, Daejeon (KR); Woo Hyun Kim, Daejeon (KR); Wan Taek Im, Daejeon (KR); Yeon Lee, Daejeon (KR)

(73) Assignees: INTELLIGENT SYNTHETIC BIOLOGY CENTER, Daejeon (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 14/431,868

(22) PCT Filed: Dec. 24, 2012

(86) PCT No.: PCT/KR2012/011402
§ 371 (c)(1),
(2) Date: Mar. 27, 2015

(87) PCT Pub. No.: WO2014/051215
PCT Pub. Date: Apr. 3, 2014

(65) Prior Publication Data
US 2015/0252337 A1 Sep. 10, 2015

(30) Foreign Application Priority Data
Sep. 27, 2012 (KR) ......... 10-2012-0108366

(51) Int. Cl.
C12N 9/10 (2006.01)
C12P 19/56 (2006.01)
C12P 33/00 (2006.01)
A01N 37/42 (2006.01)

(52) U.S. Cl.
CPC .......... *C12N 9/1051* (2013.01); *A01N 37/42* (2013.01); *C12P 19/56* (2013.01); *C12P 33/00* (2013.01); *C12Y 204/01017* (2013.01)

(58) Field of Classification Search
CPC .................................................. C12N 9/1051
USPC ......................................................... 435/193
See application file for complete search history.

(56) References Cited

U.S. PATENT DOCUMENTS 9,029,636 B2 * 5/2015 Wu ..................... C07K 14/415
435/419

FOREIGN PATENT DOCUMENTS

CN 101842112 A 9/2010
EP 2930237 A1 10/2015
WO 2009/048306 A1 4/2009
WO 2014051214 A1 4/2014

OTHER PUBLICATIONS

Jung, J.D. et al., "Discovery of genes for ginsenoside biosynthesis by analysis of ginseng expressed sequence tags," Plant Cell Rep., Oct. 1, 2003, 22:224-230.
Jung, Suk-Chae et al., "Two Ginseng UDP-Glycosyltransferases Synthesize Ginsenoside Rg3 and Rd", Plant and Cell Physiology, vol. 55, No. 12, Dec. 2014, pp. 2177-2188.
Khorolragchaa, Altanzul et al., "Grouping and characterization of putative glycosyltransferase genes from Panax ginseng Meyer", Gene, 536, No. 1, Aug. 24, 2013, pp. 186-192.
Kim, Yun-Soo et al., "Ginseng metabolic engineering: Regulation of genes related to ginsenoside biosynthesis", Journal of Medicinal Plants Research, vol. 3(13), pp. 1270-1276, Dec. 2009.
Li, Hong Y. et al., "Purification and characterization of a superoxide dismutase from Panax ginseng", Biomed. Chromatography, 2010, vol. 24, pp. 1203-1207.
Paquette, S. et al., "On the origin of family 1 plant glycosyltransferases", Phytochemistry, 62, 2003, 399-413.
Pingping, Wang et al., "Production of bioactive ginsenosides Rh2 and Rg3 by metabolically engineered yeasts", Metabolic Engineering, 29, 2015, pp. 97-105.
Shibata, Shoji, "Chemistry and Cancer Preventing Activities of Ginseng Saponins and Some Related Triterpenoid Compounds", J. Korean Med. Sci., 2001, vol. 16 (suppl), S28-37.
Strobel, Andreas, Extended European Search Report, European Patent Application No. 12885387.6, Mar. 30, 2016.
Xiang, L., "Panax notoginseng UDP-glucosyltransferase mRNA, complete cds", Database Accession No. JX018210, Jul. 31, 2012.
Xiang, L., "Full-length cDNA cloning and bioinformatics analysis of PnUGT1 gene in Panax notoginseng", Yaoxue Xuebao, vol. 47, No. 8, Aug. 2012, Abstract.
First Office Action, Japanese Application No. 2015-534374, Japanese Patent Office, May 9, 2016.
Ajikumar et al., "Isoprenoid Pathwya Optimization for Taxol Precursor Overproduction in *Escherichi coli*," Science, 330(6000):70-74, 2010.
Chen et al., "454 EST analysis detects genes putatively involved in ginsenoiside biosynthesis in Panox ginseng," Plant Cell Reports, 30(3):1593-1601, Apr. 12, 2011.
Heo, Joo Hyung, International Search Report, Korean Intellectual Property Office, PCT/KR2012/011402, Jun. 26, 2013.
Jung et al., "Identification of Novel Ginseng UDP-Glycosyltransferases Acting on C3 Position of Protopanaxdiol to Produce Ginsenosides," IFT 2012 Annual Meeting Scientific Program, Jun. 28, 2012.

(Continued)

*Primary Examiner* — Tekchand Saidha
(74) *Attorney, Agent, or Firm* — Gavrilovich, Dodd & Lindsey LLP

(57) ABSTRACT

The present invention relates to a novel uridine diphosphate (UDP)-glycosyltransferase, and particularly to a novel UDP-glycosyltransferase derived from *ginseng* and use thereof, a method for preparing glycosylated ginsenoside by converting protopanaxadiol (PPD)-type ginsenoside using the UDP-glycosyltransferase, a composition for converting the PPD-type ginsenoside into glycosylated ginsenoside, comprising the UDP-glycosyltransferase, a transformant or a culture thereof as active ingredients, a method for enhancing the expression of the UDP-glycosyltransferase using MeJA (methyl jasmonate), and a composition for enhancing the expression of the UDP-glycosyltransferase, which comprises MeJA as an active ingredient.

4 Claims, 7 Drawing Sheets

(56) References Cited

OTHER PUBLICATIONS

Kim et al., "Stimulation of Rg3 ginsenoside biosynthesis in ginseng hairy roots elicited by methyl jasmonate," 112:87-93, Aug. 26, 2012.

Luo et al., "Analysis of the transcriptome of Panax notoginseng root uncovers putative triterpene saponin-biosynthetic genes and genetic markers," MBC Genomics, 12:1-15, Dec. 23, 2011.

Ro et al., "Production of the antimalarial drug precursor artemisinic acid in engineered yeast," Nature, 440: 940-943, 2006.

Saito et al., "Triterpenoid biosynthesis and engineering in plants," Frontiers in Plant Sci., 2(25):1-8, Jun. 30, 2011.

Sun et al., "De novo sequencing and analysis of the American ginseng root transcriptome using a GS FLX Titanium platform to discover putative genes involved in ginsenoside biosynthesis," BMC Genomics, 11(262):1-12, Apr. 24, 2010.

Chinese Patent Office Action, State Intellectual Property Office of PRC, CN Appl. 201280077316.X, Jul. 6, 2016.

\* cited by examiner

Figure 1

| Ginsenosides | R₁ | R₂ |
|---|---|---|
| Rb₁ | Glc²-Glc | Glc⁶-Glc |
| Rd | Glc²-Glc | Glc |
| F₂ | Glc | Glc |
| Rg₃ | Glc²-Glc | H |
| Rh₂ | Glc | H |
| Compound K | H | Glc |
| PPD | H | H |
| Rb₂ | Glc²-Glc | Glc⁶-Ara(p) |
| Rc | Glc²-Glc | Glc⁶-Ara(f) |
| Compound MC | H | Glc⁶-Ara(f) |
| Compound Y | H | Glc⁶-Ara(p) |

| Ginsenosides | R₁ | R₂ |
|---|---|---|
| Rg₁ | Glc | Glc |
| Rh₁ | Glc | H |
| F₁ | H | Glc |
| Rf | Glc²-Glc | H |
| PPT | H | H |
| Re | Glc²-Rha | Glc |
| Rg₂ | Glc²-Rha | H |

UDP-GLYCOSYLTRANSFERASE DERIVED FROM GINSENG AND USE THEREOF

CROSS REFERENCE TO RELATED APPLICATIONS

This application is a U.S. National Stage Application filed under 35 U.S.C. §371 and claims priority to International Application No. PCT/KR2012/011402, filed Dec. 24, 2012, which application claims priority under 35 U.S.C. §119 to Korean Application No. 10-2012-0108366, filed Sep. 27, 2012, the disclosures of which are incorporated herein by reference.

TECHNICAL FIELD

The present invention relates to a novel uridine diphosphate (UDP)-glycosyltransferase, and particularly to a novel UDP-glycosyltransferase derived from *ginseng* and use thereof, a method for preparing glycosylated ginsenoside by converting protopanaxadiol (PPD)-type ginsenoside using the UDP-glycosyltransferase, a composition for converting the PPD-type ginsenoside into glycosylated ginsenoside, comprising the UDP-glycosyltransferase, a transformant or a culture thereof as active ingredients, a method for enhancing the expression of the UDP-glycosyltransferase using MeJA (methyl jasmonate), and a composition for enhancing the expression of the UDP-glycosyltransferase, which comprises MeJA as an active ingredient.

BACKGROUND

*Ginseng* (*Panax ginseng* C. A meyer) is one of the most popular medicinal herbs widely used for improving health. The root of *ginseng* was consumed as a herbal tea in a traditional medicine, and currently it has been included in a variety of products including candy, instant tea, and tonic drink. Ginsenosides which are glycosylated triterpenes contained in *ginseng* have positive effects on health. In particular, ginsenosides have been known to have various pharmacological effects such as immune system enhancement and revitalization of body functions. Also more than 40 different ginsenosides have been identified in the root of *ginseng*. However, since mass production of each of the ginsenosides is hard, it remains as a major obstacle for investigating efficacy of certain ginsenoside, for example, its therapeutic effects on specific diseases.

Ginsenosides are glycosylated dammarene-type tetracyclic triterpenes, and can be classified into three different groups based on their aglycone structure: Protopanaxadiol (PPD)-type ginsenosides, Protopanaxatriol (PPT)-type ginsenosides, and Oleanolic acid-type ginsenosides. These three groups can be further classified based on the position and number of sugar moieties (aglycones) attached to the C-3, C-6, and C-20 positions of the rings by a glycosidic bond in the chemical structure. PPD and PPT also possess different hydroxylation patterns. PPD possesses —OH groups at the C-3, C-12, and C-20 positions, whereas PPT possesses —OH groups at the C-3, C-6, C-12, and C-20 positions. PPD and PPT can be glycosylated with glucose and/or other types of sugars to be converted into various ginsenosides. The representative PPD-type ginsenosides include ginsenoside Rh2, ginsenoside Rg3, Compound K (C-K), ginsenoside F2, and ginsenoside Rd. And the representative PPT-type ginsenosides include ginsenoside F1, Rg1, Re, Rh1, and Rg2.

The biosynthetic pathway of ginsenosides is only partially identified. The ginsenoside biosynthesis is known to share the biosynthetic pathways with other triterpenes until oxidosqualene is synthesized by a series of condensation reactions of isopentenyl diphosphate and DMADP (dimethylallyl diphosphate) by the action of IPP isomerase (IPI), GPP synthase (GPS), FPP synthase (FPS), squalene synthase (SS) and squalene epoxidase (SE) (Ajikumar et al. Science, 330, 70-74. 2010; Ro et al. Nature, 440, 940-943. 2006; Sun et al. BMC genomics, 11, 262, 2010). Oxidosqualene is cyclized into dammarenediol-II by DS (dammarenediol-II synthase) which is a triterpene cyclase. Dammarenediol-II has hydroxyl groups at the C-3 and C-20 positions, and is converted into PPD by hydroxylation of the C-12 position by a p450 enzyme, PPDS (protopanaxadiol synthase). PPDS can be also converted into PPT by hydroxylation at the C-6 position by another p450 enzyme, PPTS (protopanaxatriol synthase). PPD can be converted into PPD-type ginsenoside by glycosylation at the C-3 and/or C-20 position(s), and PPT can be converted into PPT-type ginsenoside by glycosylation at the C-6 and/or C-20 position(s). UDP (Uridine diphosphate)-glycosyltransferase (UGT) is considered to be involved in synthetic pathways of various ginsenosides by formation of O-, β1,2-, or β1,6-glycosidic linkage. DS, PPDS and PPTS have been reported as the enzymes involved in ginsenoside biosynthesis, but it has not been identified whether UGT is involved in the biosynthesis of ginsenosides.

UDP-glycosyltransferase is an enzyme that catalyzes the transfer of a sugar moiety from UDP-sugar to a wide range of metabolites such as hormones and secondary metabolites. Generally, UGT acts in the final step of biosynthetic pathway in order to increase solubility, stability, storage, bioactivity, or biological availability of metabolites. As recognized by a remarkable diversity of metabolites in plants, the genome of a plant possesses hundreds of different UGTs. For example, a plant model, *Arabidopsis thaliana* contains 107 UGTs that belong to 14 different groups (Group A to Group N) based on the amino acid sequence. Different UGTs show substrate specificity towards both sugar donor and sugar acceptor. For example, UGT78D2 transfers glucose from UDP-glucose to the C-3 position of flavonol (kaempferol, quercetin) and anthocyanin (cyanidin) in order to produce flavonol 3-O-glucosides and cyanidin 3-O-glucoside, respectively. It seems that such glycosylation is essential for in vivo stability and storage of the compound. On the other hand, UGT89C1 transfers rhanmnose from UDP-rhanmnose to the C-7 position of flavonol-3-O-glucosides in order to produce flavonol-3-O-glucoside-7-O-rhamnoside. Likewise, UGT89C1 does not utilize UDP-glucose and anthocyanin-3-O-glucoside as a substrate. And it has different specificity towards UDP-sugar and acceptor from that of UGT78D2. Therefore, there is a need to investigate the substrate specificity for different types of UGTs.

DISCLOSURE

Technical Problem

The present inventors put a lot of effort into development of a novel UDP-glycosyltransferase with a substrate specificity and regioselectivity to be used for biosynthesis of a particular ginsenoside. As a result, the present inventors identified a novel glycosyltransferase called PgUGT74A1 from *ginseng*, and they found that PgUGT74A1 has an activity of converting PPD and C-K into ginsenoside Rh2 and ginsenoside F2, respectively by specifically acting on the PPD-type ginsenosides, PPD and C-K, to catalyze O-glycosylation at the C-3 position. Having this activity, PgUGT74A1 can be used for the production of certain glycosylated ginsenoside.

Technical Solution

An object of the present invention is to provide a novel uridine diphosphate (UDP)-glycosyltransferase protein derived from *ginseng*.

Another object of the present invention is to provide a polynucleotide encoding the UDP-glycosyltransferase protein, an expression vector comprising the polynucleotide, and a transformant introduced with the expression vector.

Still another object of the present invention is to provide a method for preparing the UDP-glycosyltransferase protein.

Still another object of the present invention is to provide a method for preparing a glycosylated ginsenoside by converting a protopanaxadiol (PPD)-type ginsenoside using the UDP-glycosyltransferase protein, the transformant or a culture thereof.

Still another object of the present invention is to provide a composition for converting a PPD-type ginsenoside into a glycosylated ginsenoside, comprising the UDP-glycosyltransferase protein, the transformant or the culture thereof as an active ingredient.

Still another object of the present invention is to provide a method for enhancing expression of the UDP-glycosyltransferase using MeJA (methyl jasmonate).

Still another object of the present invention is to provide a composition for enhancing expression of the UDP-glycosyltransferase, comprising MeJA as an active ingredient.

Advantageous Effects

The novel UDP-glycosyltransferase of the present invention has a substrate specificity and regioselectivity, and thus it is able to transfer a sugar moiety specifically to the C-3 position of a PPD-type ginsenoside. Therefore it is useful for mass production of a particular ginsenoside such as ginsenoside Rh2, F2, Rg3 or Rd.

DESCRIPTION OF DRAWINGS

FIG. 1 shows chemical structures of PPD-type and PPT-type ginsenosides;

FIG. 3a shows the result of TLC analysis of PgUGT74A1 of the present invention and 10 different ginsenosides (right panel: treated with PgUGT74A1, left panel: untreatment), and each of the 10 different ginsenosides was reacted with PgUGT74A1 in the presence of UDP-glucose (UDP-Glc). As shown in FIG. 3a, PgUGT74A1 converted only PPD and C-K among 10 ginsenosides into Rh2 and F2 respectively, (triangles). FIG. 3b shows the result of High performance liquid chromatography (HLPC) of the products from the reaction of PPD (left) and C-K (right) with PgUGT74A1 of the present invention. Rh2 and F2 converted from PPD and C-K respectively are marked as triangles;

FIG. 4a shows the result of TLC analysis of PgUGT94B1 of the present invention and 10 different ginsenosides (right panel: treated with PgUGT94B1, left panel: untreated). Each of the 10 different ginsenosides was reacted with PgUGT94B1 in the presence of UDP-glucose (UDP-Glc). As shown in FIG. 4a, PgUGT94B1 converted only ginsenoside Rh2 and ginsenoside F2 among 10 ginsenosides into ginsenoside Rg3 and ginsenoside Rd respectively (triangles). FIG. 4b is the result of HPLC analysis of products from the reaction of ginsenoside Rh2 (left) and ginsenoside F2 (right) with PgUGT94B1 of the present invention. Ginsenoside Rg3 and ginsenoside Rd converted from ginsenoside Rh2 and ginsenoside F2 respectively are marked as triangles;

FIG. 6a shows the expression level of ginsenoside biosynthetic genes in the leaf and root of *ginseng*, and FIG. 6b shows changes in the expression level of ginsenoside biosynthetic genes in the leaf after treated with MeJA (Methyl jasmonate). MeJA was sprayed on the leaf everyday for a total of 5 days, and on the 6th day after the start of the treatment, samples were collected for the expression analysis. FIG. 6c shows the changes in the expression level of ginsenosides after treatment with MeJA. Error bars show a standard deviation (SD) of three biological replicates.

BEST MODE

Figure 2:
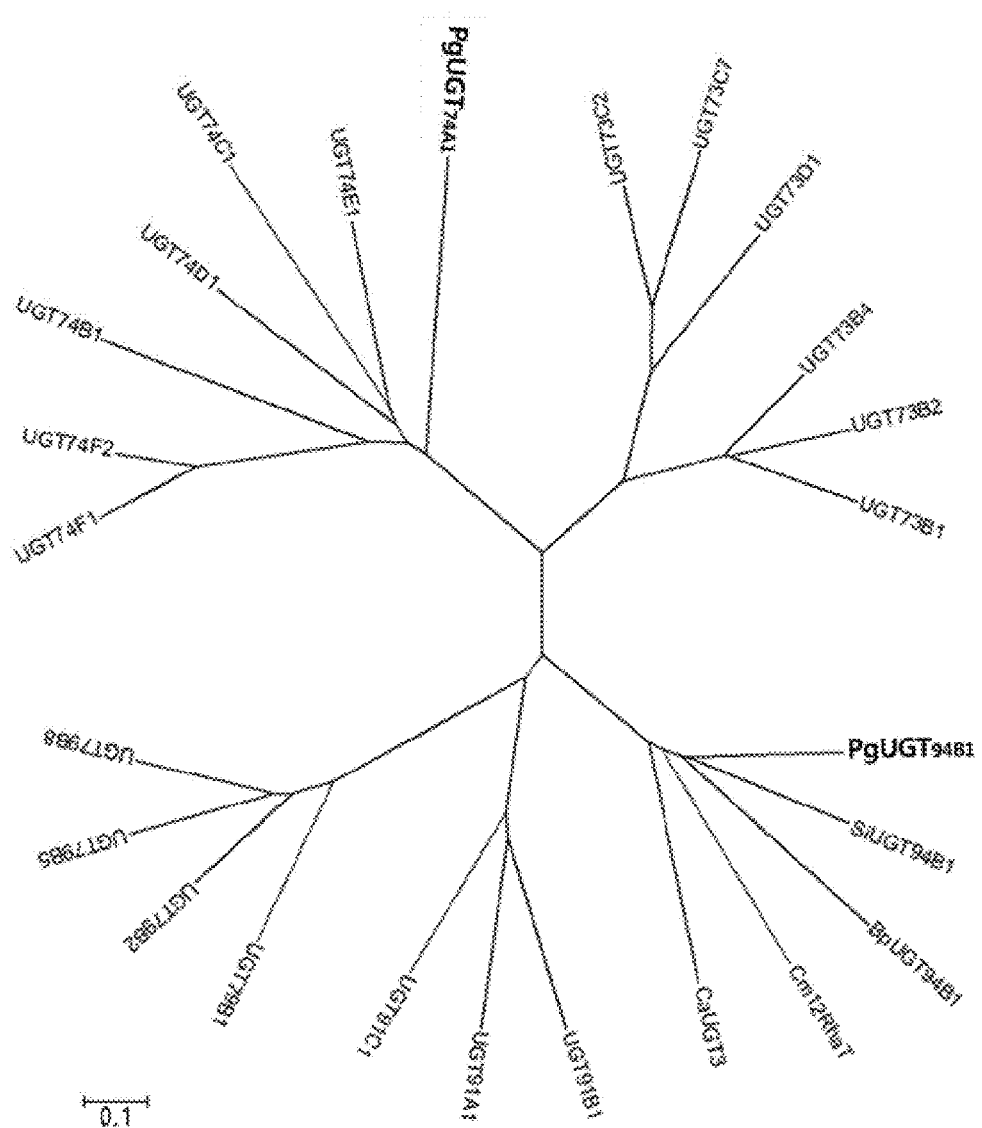
FIG. 2 shows a schematic diagram for clustering between each of the UDP-glycosyltransferases, PgUGT74A1 and PgUGT94B1, with UGT74 and UGT94, respectively. Amino acid sequences of UGTs were aligned by using MEGA5 software, and the alignment is demonstrated as a neighbor-joining tree. All USTs except for PgUGTs (*ginseng, Panax ginseng*), SiUGT94B1 (*Sesamumindicum* L.), BpUGT94B1 (*Bellis perennis*), Cm1, 2RhaT (*Citrus maxima*) and CaUGT3 (*Catharanthus roseus*) are derived from *Arabidopsis thaliana*.

As one aspect, the present invention provides a novel uridine diphosphate (UDP)-glycosyltransferase (UGT) derived from *ginseng*.

As used herein, the term "uridine diphosphate (UDP)-glycosyltransferase" is an enzyme that catalyzes the transfer of a monosaccharide moiety from a glycosyl donor to a glycosyl acceptor molecule, and in particular, it refers to an enzyme that utilizes UDP-sugar as the glycosyl donor. In the present invention, the UDP-glycosyltransferase may be interchangeably used with UGT. It is thought that the UDP-glycosyltransferase catalyzes various glycosylations of protopanaxadiol (PPD) and protopanaxatriol (PPT) to generate a wide range of ginsenosides. However, even those enzymes with have the UDP-glycosyltransferase activity have different substrate specificity and regioselectivity depending on the type of the enzyme. Therefore, it needs to be determined whether the enzyme is a UDP-glycosyltransferase specifically acting on ginsenoside which is a *ginseng* saponin. There has been no report on UDP-glycosyltransferase derived from *ginseng*, which specifically acts at the C-3 position of the PPD-type ginsenoside and transfers a sugar moiety in order to produce ginsenoside Rh2 or F2 from PPD or Compound K (C-K). The UDP-glycosyltransferase was identified for the first time by the present inventors.

For the purpose of the present invention, the UDP-glycosyltransferase may be an UDP-glycosyltransferase derived from *ginseng*, preferably a UDP-glycosyltransferase derived from *Panax ginseng*, and more preferably a UDP-glycosyltransferase represented by the amino acid sequence of SEQ ID NO. 1, but is not limited thereto. In one example of the present invention, the UDP-glycosyltransferase represented by the amino acid sequence of SEQ ID NO. 1 is designated as PgUGT74A1.

The UDP-glycosyltransferase may refer to the proteins possessing the amino acid sequence of SEQ ID NO.1, but also an amino acid sequence having a sequence homology of 70% or higher, preferably 80% or higher, more preferably 90% or higher, even more preferably 95% or higher, even much more preferably 98% or higher, and most preferably 99% or higher to the amino acid sequence of SEQ ID NO. 1. However, any protein can be used without limitation, as long as it has the UDP-glycosyltransferase activity being capable of substantially transferring a sugar to *ginseng* ginsenoside. In addition, if the protein with the above sequence homology has substantially the same or corresponding bioactivity as UDP-glycosyltransferase even the variants of the protein having a portion of amino acid sequence deleted, modified, substituted, or added may be included in the scope of the present invention.

As used herein, the term "homology" is intended to indicate the degree of similarity to the amino acid sequence of a wild type protein or a nucleotide sequence that encodes the same, and includes sequences having homology of the above percentage or higher with the amino acid sequence or base sequence of the present invention. Homology comparisons can be conducted by sight or by readily available sequence comparison programs.

Preferably, the UDP-glycosyltransferase of the present invention refers to a protein having an activity of converting a PPD-type ginsenoside into a glycosylated ginsenoside, but is not limited thereto.

As used herein, the term "PPD-type ginsenoside" is a dammarane-type saponin, and it means a ginsenoside having two hydroxyl groups (—OH) at its non-sugar component (aglycone), and examples thereof include PPD (protopanaxadiol), Rb1, Rb2, Rb3, Rc, Rd, Ra3, Rg3, Rh2, Rs1, C—O, C—Y, C-Mc1, C-Mc, F2, C-K, Gypenoside XVII, Gypenoside LXXV, and Rs2. For the purpose of the present invention, the PPD-type ginsenoside may be any ginsenoside without limitation, as long as it is a ginsenoside that can be glycosylated by the UDP-glycosyltransferase of the present invention. It may be preferably a ginsenoside to be O-glycosylated, more preferably a ginsenoside to be glycosylated at its C-3 position, and much more preferably PPD or C-K, but is not limited thereto. In one example of the present invention, PPD and Compound K were used as the PPD-type ginsenoside that can be glycosylated by the UDP-glycosyltransferase of the present invention, PgUGT74A1. A schematic diagram for the structure of the ginsenoside is shown in FIG. 1.

As used herein, the term "glycosylated ginsenoside" means a ginsenoside having a monosaccharide or larger saccharide molecule attached to the hydroxyl group of the non-sugar component (aglycone) that constitutes the ginsenoside, and exemplified by ginsenoside Rh2, Rg3, F2 or Rd, but is not limited thereto. For the purpose of the present invention, the glycosylated ginsenoside includes any glycosylated ginsenoside without limitation, as long as it is a ginsenoside glycosylated by the UDP-glycosyltransferase of the present invention. The glycosylated ginsenoside preferably means a ginsenoside having an O-glycosidic bond, and more preferably a ginsenoside having a sugar of monosaccharide or higher saccharide at its C-3 position, but is not limited thereto. In one example of the present invention, PPD and Compound K (C-K) were converted into glycosylated ginsenosides, ginsenoside Rh2 and F2 by the activity of PgUGT74A1, respectively.

In particular, the UDP-glycosyltransferase of SEQ ID NO. 1 in the present invention transfers a glucose from UDP-glucose to the hydroxyl group (—OH) at the C-3 position of PPD-type ginsenoside forming an O-glycosidic bond, thereby producing glycosylated ginsenoside.

Specifically, the UDP-glycosyltransferase transfers the glucose moiety from UDP-glucose to the hydroxyl group at the C-3 position of PPD to form the O-glycosidic bond, thereby converting PPD into ginsenoside Rh2. The UDP-glycosyltransferase transfers the glucose moiety from UDP-glucose to the hydroxyl group at the C-3 position of C-K forming the O-glycosidic bond, thereby converting C-K into ginsenoside F2. On the other hand, the UDP-glycosyltransferase does not act on the hydroxyl group at the C-12 or C-20 position of PPD-type ginsenoside, but specifically transfers a sugar to the hydroxyl group at the C-3 position. In addition, even though PPT-type ginsenoside has the hydroxyl group at the C-3 position, the UDP-glycosyltransferase of the present invention does not act on the PPT-type ginsenoside. Therefore, since the UDP-glycosyltransferase of the present invention has a substrate specificity and regioselectivity for PPD-type ginsenosides, particularly the hydroxyl group at the C-3 position of PPD and C-K, it can be used for conversion of a particular ginsenoside, preferably conversion of PPD and C-K into Rh2 and F2 respectively.

Figure 3:
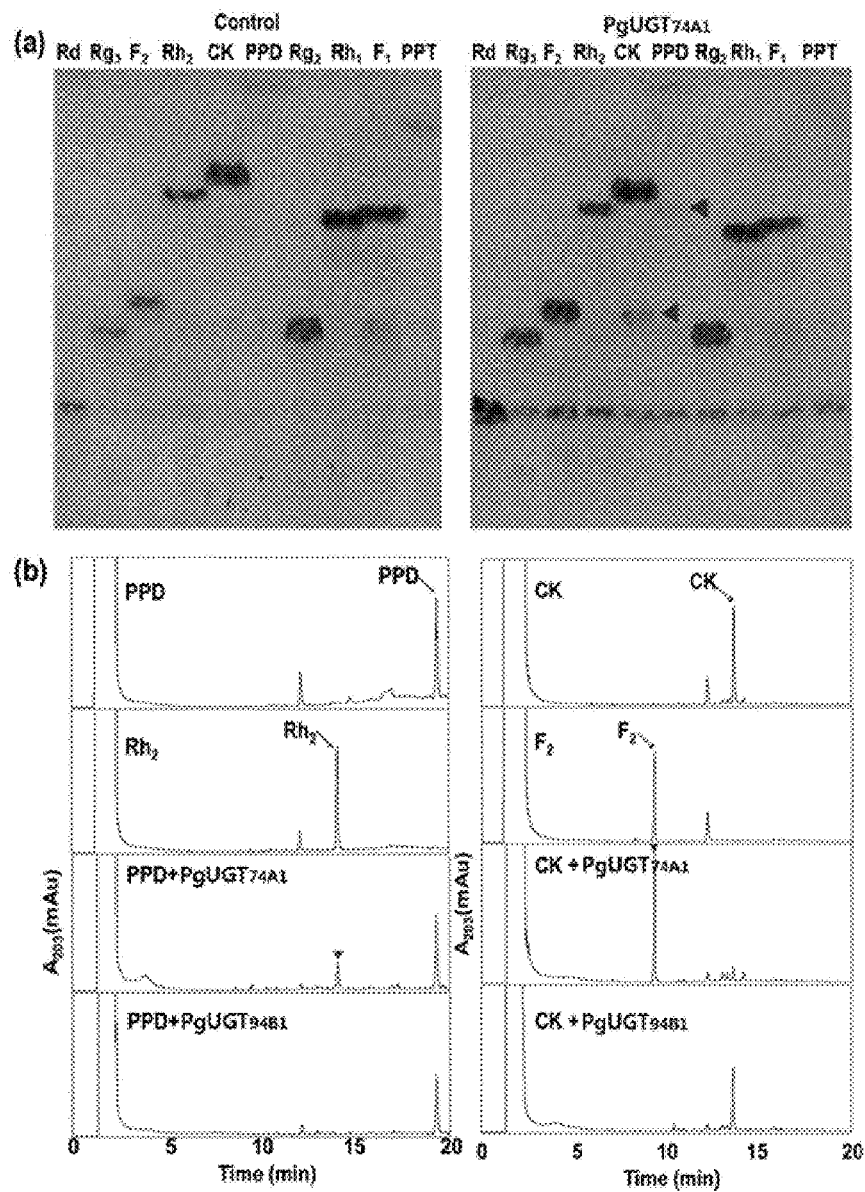
FIG. 3A-B shows the results of thin-layer chromatography (TLC) demonstrating that the UDP-glycosyltransferase, PgUGT74A1 has an activity of converting PPD into ginsenoside Rh2 and converting Compound K into ginsenoside F2.
Figure 7:
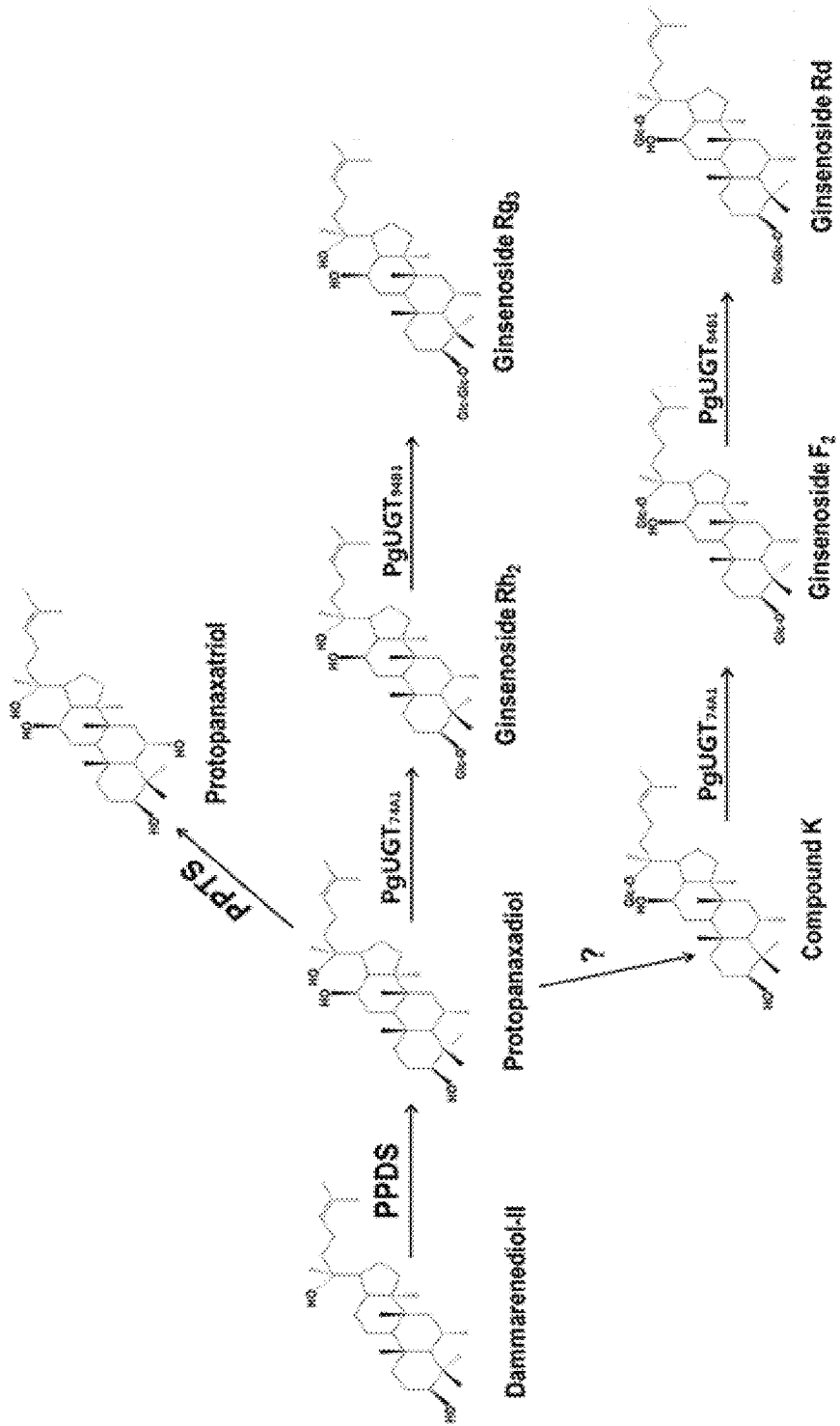
FIG. 7 is the schematic diagram for the ginsenoside biosynthetic pathway of Rg3 and Rd, involving UDP-glycosyltransferase of the present invention.

In one example of the present invention, the novel UDP-glycosyltransferase, PgUGT74A1 was newly isolated from *ginseng* (Example 1), and the result of the sequence analysis showed that the glycosyltransferase was clustered in the UGT74 family, but was not clustered in the *Arabidopsis thaliana* UGT74 subfamily (Experimental Example 1 and FIG. 2). In addition, the glycosyltransferase regioselectively acts on PPD-type ginsenosides and transfers one glucose to the hydroxyl group at the C-3 position, thereby producing glycosylated ginsenosides (Experimental Examples 2 and 4; and FIGS. 3 and 5). The enzymatic activity of PgUGT74A1 protein is shown in FIG. 7.

As another aspect, the present invention provides a polynucleotide encoding the UDP-glycosyltransferase, an expression vector comprising the polynucleotide, and a transformant comprising the expression vector therein.

The UDP-glycosyltransferase is the same as described above.

The polynucleotide that encodes the UDP-glycosyltransferase may be preferably a polynucleotide represented by a nucleotide sequence of SEQ ID NO. 2, and also includes any nucleotide sequence having a sequence homology of 70% or higher, preferably 80% or higher, more preferably 90% or higher, much more preferably 95% or higher, and most preferably 98% or higher to the nucleotide sequence of SEQ ID NO. 2 without limitation, as long as it is able to substantially encode a protein having the UDP-glycosyltransferase activity.

The expression vector comprising the polynucleotide of the present invention is an expression vector capable of expressing the target protein in a suitable host cell, and refers to a DNA construct comprising essential regulatory elements which are operably linked to express a nucleic acid insert. The target proteins can be obtained by transformation or transfection of the prepared recombinant vector into the host cells.

The expression vector comprising the polynucleotide provided in the present invention includes, but is not limited to, *E. coli*-derived plasmids (pYG601BR322, pBR325, pUC118 and pUC119), *Bacillus subtilis*-derived plasmids (pUB110 and pTP5), yeast-derived plasmids (YEp13, YEp24 and YCp50) and Ti-plasmids used in *Agrobacterium*-mediated transformation. The specific example of phage DNA includes λ-phage (Charon4A, Charon21A, EMBL3, EMBL4, λgt10, λgt11 and λZAP). Further, an animal virus such as retrovirus, adenovirus or vaccinia virus, an insect virus such as baculovirus, a double-stranded plant virus (e.g., CaMV), a single-stranded virus, or a viral vector originated from Geminivirus may be used.

Moreover, as the vector of the present invention, a transcriptional activator, such as B42-linked fusion plasmid (e.g., pJG4-5), may be used. In order to facilitate purification of the target protein obtained in the present invention, the plasmid vector may further include other sequences, if necessary. The fusion plasmid may include a tag such as GST, GFP, His-tag, Myc-tag or the like, but the fusion plasmid of the present invention is not limited to these examples. In one example of the present invention, pGEX4T-1 which is a GST gene-fused vector was used for construction of the expression vector that comprises the UDP-glycosyltransferase-encoding polynucleotide.

In addition, the fusion protein expressed by the vector comprising the fusion sequence may be purified by affinity chromatography. For example, if a glutathione-S-transferase is to be fused with other sequence, glutathione which is a substrate of the enzyme can be used. If hexa-histidine is used as a tag to the target protein, the target protein can be easily purified by using a Ni-NTA His-bind resin column (Novagen, USA).

For insertion of the polynucleotide of the present invention into the vector, the purified DNA may be cleaved using appropriate restriction enzymes, and inserted into the restriction sites or cloning site of a suitable vector DNA.

The polynucleotide encoding the UDP-glycosyltransferase of the present invention may be operably linked to a vector. The vector of the present invention may further include cis elements such as an enhancer, a splicing signal, a poly A addition signal, a selection marker, a ribosome binding sequence (SD sequence), in addition to a promoter and the nucleic acid of the present invention. As examples of the selection marker, chloramphenicol resistance gene, ampicillin resistance gene, dihydrofolate reductase, neomycin resistance gene or the like can be used, but the type of additional elements to be operably linked is not limited to these examples.

As used herein, the term "transformation" means an introduction of DNA into a host cell such that the DNA can be replicated as an extra-chromosomal element or by chromosomal integration. That is, transformation refers to synthetic alteration of genes by introducing a foreign DNA into the cell.

The transformation of the present invention may be performed by any transformation method, and can be easily performed following the common method known in the art. In general, examples of the transformation methods include a CaCl2 precipitation, a Hanahan method that is an improved CaCl2 method by using DMSO (dimethyl sulfoxide) as a reducing material, electroporation, calcium phosphate precipitation, protoplast fusion, agitation using silicon carbide fiber, *Agrobacterium*-mediated transformation, PEG-mediated transformation, dextran sulfate-, lipofectamine-, and desiccation/inhibition-mediated transformation. The method for transformation of the vector comprising the polynucleotide that encodes UDP-glycosyltransferase of the present invention is not limited to these examples, and the transformation or transfection methods typically used in the art may be used without limitation.

In the present invention, the type of host cell is not particularly limited, as long as it is able to express the polynucleotide of the present invention. The specific examples of the host cell to be used in the present invention include bacteria belonging to the genus *Escherichia* such as *E. coli*; bacteria belonging to the genus *Bacillus* such as *Bacillus subtilis*; bacteria belonging to the genus *Pseudomonas* such as *Pseudomonas putida*; yeasts such as *Saccharomyces cerevisiae* and *Schizosaccharomyces pombe*; animal cells, plant cells and insect cells. The specific examples of the *E. coli* strain to be used in the present invention include CL41 (DE3), BL21, and HB101, and the specific examples of the *Bacillus subtilis* strain include WB700 and LKS87. The type of the plant transformant introduced with the expression vector comprising the polynucleotide of the present invention is not particularly limited, as long as it is able to express the glycosyltransferase of the present invention. Examples thereof include tobacco, *Arabidopsis thaliana*, potato, ginseng, sesame, citron, *Bellis* or the like, but are not limited thereto.

Any promoter can be used as a promoter of the present invention, as long as it is able to drive expression of the nucleic acid of the present invention in the host cell. For example, *E. coli*- or phage-derived promoters such as trp promoter, lac promoter, PL promoter, and PR promoter; *E. coli* infection phage-derived promoters such as T7 promoter, CaMV35S, MAS or histone promoter may be used. Synthetically modified promoters such as tac promoter may be also used.

The transformant that is introduced with the expression vector comprising the polynucleotide which encodes the UDP-glycosyltransferase protein of the present invention by the above method has a bioactivity of transferring a glucose by formation of O-glycosidic bond at the C-3 position of PPD-type ginsenoside. Preferably, the transformant means a transformant having capable capability of converting ginsenoside PPD into ginsenoside Rh2 or converting C-K into ginsenoside F2, but is not limited thereto.

As another aspect, the present invention provides a method for preparing the UDP-glycosyltransferase protein.

The UDP-glycosyltransferase is the same as described above.

Preferably, the preparation method comprises (a) culturing the transformant that is introduced with the vector comprising the polynucleotide that encodes the UDP-glycosyltransferase; (b) producing UDP-glycosyltransferase from the cultured transformant; and (c) recovering the produced UDP-glycosyltransferase.

Culturing of the transformant can be carried out by following a common method used in the art. A carbon source included in the growth medium for transformant may be selected by those skilled in the art according to the type of the transformant. And a suitable condition for culturing may be adopted in order to adjust the culturing time and amount.

As another aspect, the present invention provides a method for preparing a glycosylated ginsenoside by converting a PPD (protopanaxadiol)-type ginsenoside using the UDP-glycosyltransferase, the transformant or the culture thereof.

The UDP-glycosyltransferase, transformant, PPD-type ginsenoside, and glycosylated ginsenoside are the same as described above.

To be more specific, the method comprises the step of reacting the PPD-type ginsenoside with an UDP-glycosyltransferase protein represented by the amino acid sequence of SEQ ID NO. 1, a transformant introduced with an expression vector comprising a polynucleotide that encodes the protein, or a culture of the transformant in the presence of UDP-sugar.

As used herein the term "culture of the transformant" means a product obtained by culturing the transformant according to the known method of culturing microorganisms. The culture includes the UDP-glycosyltransferase of SEQ ID NO. 1 of the present invention, and thus it is capable of converting PPD-type ginsenosides into glycosylated ginsenosides, for example, conversion of ginsenoside PPD into ginsenoside Rh2, or conversion of Compound K into ginsenoside F2.

As the PPD-type ginsenoside used as a starting material in the present invention, isolated and purified ginsenoside, or ginsenoside included in a powder or extract of *ginseng* may be used. That is, a powder or extract of *ginseng* comprising ginsenoside may be directly used as a starting material to perform the method of the present invention. The *ginseng* used in the present invention includes the known various types of ginsengs, such as *Panax ginseng, P. quiquefolius, P. notoginseng, P. japonicus, P. trifolium, P. pseudoginseng* and *P. vietnamensis*, but is not limited thereto.

Preferably, the conversion may occur through bioconversion of the PPD-type gisenoside into a glycosylated ginsenoside by UDP-glycosyltransferase of the present invention, transformant introduced with the expression vector comprising the polynucleotide that encodes the UDP-glycosyltransferase, or culture of the transformant, and it may be achieved by transferring sugar to hydroxyl group (—OH) at the C-3 position of ginsenosides. The protein represented by the amino acid sequence of SEQ ID NO. 1 of the present invention is able to convert a PPD-type ginsenoside having hydroxyl group at C-3 position, preferably PPD or C-K, into a glycosylated ginsenoside. The bioconversion by the protein represented by the amino acid sequence of SEQ ID NO. 1 of the present invention includes conversion of PPD into Rh2, and conversion of C-K into F2. Thus, the method of the present invention can be used in the fields that require glycosylated ginsenosides, in particular, ginsenoside Rh2 or F2.

The method for preparing glycosylated ginsenoside may further comprise the step of reacting the PPD-type ginsenoside with the UDP-glycosyltransferase protein which is represented by the amino acid sequence of SEQ ID NO. 3, transformant introduced with the vector comprising the polynucleotide that encodes the protein, or culture of the transformant in the step of reacting PPD-type ginsenoside with the UDP-glycosyltransferase of SEQ ID NO. 1, transformant introduced with the vector comprising the polynucleotide that encodes the UDP-glycosyltransferase of SEQ ID NO. 1, or culture of the transformant.

As used herein, the term "UDP-glycosyltransferase represented by the amino acid sequence of SEQ ID NO. 3" means an enzyme that is capable of transferring a sugar moiety from UDP-sugar to ginsenoside by formation of β1,2 glycosidic linkage. The UDP-glycosyltransferase represented by the amino acid sequence of SEQ ID NO. 3 has capable capability of transferring a sugar moiety from the sugar donor such as UDP-sugar to the sugar acceptor like 3-O-glucosylated ginsenoside so as to cause formation of β1,2 glycosidic bond. Thus, it converts 3-O-glucosylated ginsenoside into glycosylated ginsenoside. The UDP-glycosyltransferase represented by the amino acid sequence of SEQ ID NO. 3 is a glycosyltransferase derived from *ginseng*, which was isolated for the first time by the present inventors, and can be interchangeably used with PgUGT94B1 in the present invention.

The sugar acceptor of the UDP-glycosyltransferase represented by the amino acid sequence of SEQ ID NO. 3 is 3-O-glucosylated ginsenoside, and preferably ginsenoside Rh2 or F2, but is not limited thereto. Therefore, since the glycosyltransferase has an activity of transferring a sugar moiety by formation of β1,2 glycosidic linkage with the O-glucoside at the C-3 position of ginsenoside Rh2, it is able to convert ginsenoside Rh2 into ginsenoside Rg3. Likewise, since the glycosyltransferase has an activity of transferring a sugar moiety by formation of β1,2 glycosidic linkage with the O-glucoside at the C-3 position of ginsenoside F2, it is able to convert ginsenoside F2 into Rd.

Figure 5:
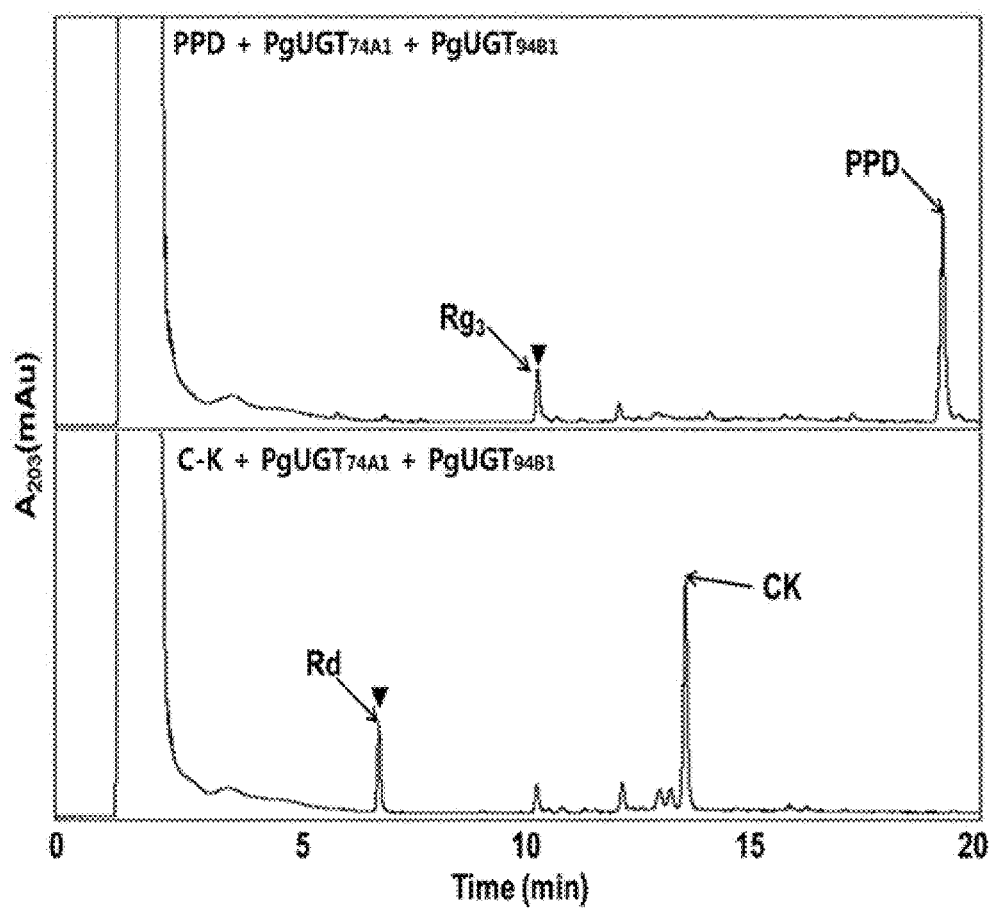
FIG. 5 shows HPLC analysis results demonstrating that if both of PgUGT74A1 and PgUGT94B1 are used, PPD and C-K were converted into ginsenoside Rg3 and Rd respectively. PPD (upper panel) or C-K (lower panel) was incubated with both of PgUGT74A1 and PgUGT94B1 in the presence of UDP-Glc. Then the reaction mixture was analyzed by HPLC. The result showed that PPD and C-K were converted into Rg3 and Rd respectively. Rg3 and Rd converted by the above two enzymes are marked as black triangles.

Thus, if both of the UDP-glycosyltransferase that specifically acts on the hydroxyl group at the C-3 position of PPD-type ginsenoside and UDP-glycosyltransferase represented by the amino acid sequence of SEQ ID NO.3 are used, PPD can be converted into ginsenoside Rh2, which in turn can be converted into Rg3. Through this process, PPD can be converted into ginsenoside Rg3. If C-K is used as a starting material, C-K is converted into ginsenoside F2 by the glycosyltransferase of the present invention, which in turn is converted into ginsenoside Rd. Through this process, C-K is converted into ginsenoside Rd. In one example of the present invention, both PgUGT74A1 and PgUGT94B1 were used to convert PPD into ginsenoside Rg3 and convert C-K into ginsenoside Rd. Thus, it was confirmed that both of the above enzymes can be used to produce ginsenoside Rg3 and Rd with high yield (FIG. 5).

As another aspect, the present invention provides a composition for converting a PPD (protopanaxadiol)-type ginsenoside into a glycosylated ginsenoside, which comprises the UDP-glycosyltransferase protein represented by the amino acid sequence of SEQ ID NO. 1, transformant or culture thereof as an active ingredient.

The UDP-glycosyltransferase, the transformant, and culture thereof; and the conversion of PPD-type ginsenoside into glycosylated ginsenoside are the same as described above.

The composition may further comprise the UDP-glycosyltransferase which is represented by the amino acid sequence of SEQ ID NO. 3, the transformant transfected with the vector comprising the polynucleotide that encodes the UDP-glycosyltransferase of SEQ ID NO. 3, or the culture of the transformant.

The UDP-glycosyltransferase represented by the amino acid sequence of SEQ ID NO. 1 of the present invention transfers one sugar moiety selectively to the hydroxyl group at the C-3 position of PPD-type ginsenoside, and thus it can be used for the production of ginsenoside glycosylated at the C-3 position such as ginsenoside Rh2 or F2.

As another aspect, the present invention provides a method for enhancing expression of the UDP-glycosyltransferase in *ginseng*, comprising treating *ginseng* with a compound called methyl jasmonate (MeJA).

The UDP-glycosyltransferase is the same as described above.

As used herein, the term "MeJA (methyl jasmonate)" is a volatile organic compound involved in a plant defense and various growth pathways such as root growth. MeJA can be interchangeably used with Methyl (1R,2R)-3-Oxo-2-(2Z)-2-pentenyl-cyclopentaneacetate, and has the following Chemical structure.

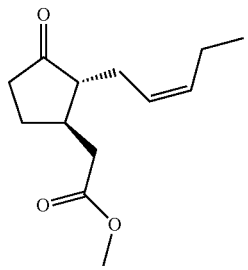

[Chemistry Formula 1]

Figure 6:
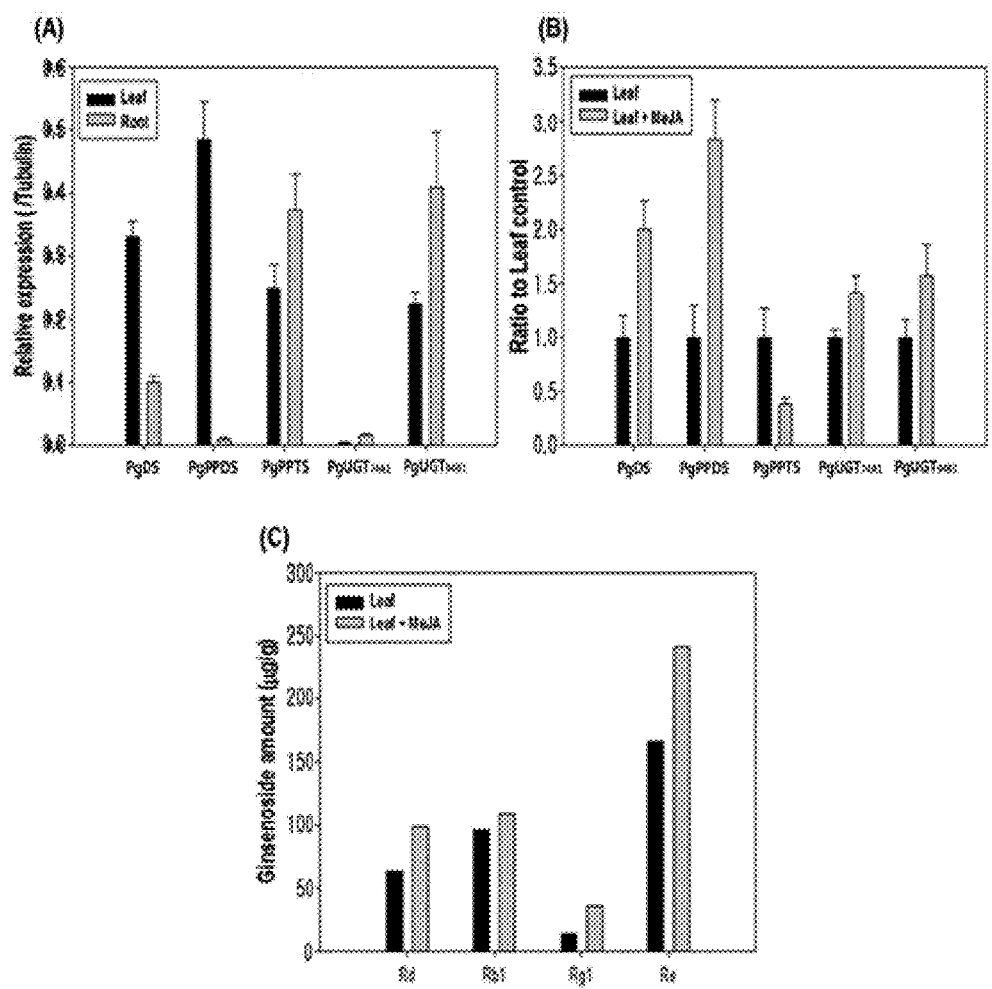
FIG. 6A-C shows the relative expression level of PgUGT74A1 and PgUGT94B1.

For the purpose of the present invention, MeJA refers to a compound capable of enhancing expression of PgUGT74A1. When MeJA is sprayed onto the leaves of *ginseng*, PgUGT74A1 expression is enhanced. Therefore, since expression of PgUGT74A1 of the present invention is increased in *ginseng* by using MeJA, MeJA is useful for the production of ginsenosides. In one example of the present invention, it was found that PgUGT74A1 expression can be remarkably increased by the treatment with MeJA (FIG. 6B).

As another aspect, the present invention provides a composition for enhancing expression of the UDP-glycosyltransferase, which comprises MeJA as an active ingredient.

MeJA and UDP-glycosyltransferase are the same as describe above.

In addition, MeJA is able to increase expression of the PgUGT74A1 of the present invention, and thus the composition comprising MeJA as an active ingredient of the present invention can be used for enhancing the PgUGT74A1 expression, and preferably applied to *ginseng* so as to increase the PgUGT74A1 expression in *ginseng*.

Mode for Invention

The present invention is described in more details through providing Examples as below. However these Examples are merely meant to illustrate, but in no way to limit, the claimed invention.

Example 1

Cloning and Purification of *Ginseng* UDP-Glycosyltransferase (PgUGT)

Two types of UGT genes identified from the *ginseng* EST library were cloned into a pGEX4T-1 vector using the primer sets listed in the following Table 1 (SEQ ID NOs. 5 and 6, SEQ ID NOs. 7 and 8), and designated as PgUGT74A1 and PgUGT94B1, respectively.

TABLE 1

| Primer | Sequence (5'->3') | SEQ ID NO |
|---|---|---|
| PgUGT74A1-BamHI | AGGCATGGATCCCTGAGCAAAACTCACATTATGTTCATC | 5 |
| PgUGT74A1-EcoRI | AGGCATGAATTCTCAGGAGGACACAAGCTTTGAAATGAACTC | 6 |
| PgUGT94B1-BamHI | AGGCATGGATCCGATAACCAAAAAGGTAGAATCAGTATA | 7 |
| PgUGT94B1-EcoRI | AGGCATGAATTCCTATTGTTCATCTTTCTTCTTCTTACAAAT | 8 |

The *E. coli* cells (*E. coli* BL21-CodonPlus (DE3)-RIL) transfected with the recombinant proteins, PgUGT74A1 and PgUGT94B1, were cultured in a LB medium supplemented with 50 μg/ml ampicillin and 34 μg/ml chloramphenicol. Then the proteins were purified from the cell culture.

The expression of the target gene was induced by using 0.1 mM IPTG. Then the cell pellet was isolated by centrifuging the cell culture at 2,500 g at 4° C. for 15 minutes. The collected cell pellet was resuspended in 10 mM PBS buffer (pH 7.0), and the cells were disrupted by ultrasonication (Vibra-cell, Sonics&Matreials, CT). Non-disrupted cells and cell debris were removed by centrifugation of the sample at 10,000 g at 4° C. for 15 minutes, and the resulting supernatant was purified further by being passed through a syringe filter with a pore size of 0.45 μm. The recombinant proteins were purified from a cell-free extract by glutathione-sepharose affinity chromatography (GE Healthcare).

Example 2

In vitro Enzyme Assay

A glycosyltransferase assay was performed in a reaction buffer (10 mM PBS buffer, pH 7) containing the purified PgUGT74A1 or PgUGT94B1 (30 μg), a ginsenoside compound (5 mM) and UDP-glucose (50 mM). For this assay, 10 different types of ginsenosides including PPD (Protopanaxadiol), PPT (Protopanaxatriol), Compound K (C-K), ginsenoside Rg3, Rh2, F2, Rd, Rg2, Rh1 and F1 were used, and the structures of the ginsenosides are shown in FIG. 1.

The reaction mixture was incubated at 35° C. for 12 hours, and then the products were analyzed by thin-layer chromatography (TLC) or high performance liquid chromatography (HPLC).

TLC analysis was performed using a mobile phase (acetone:methanol:DDW=65:35:10 vol/vol) and a $60F_{254}$ silica gel plate (Merck, Germany). The resolved product on the TLC plate was detected by spraying the plate with 10% (vol/vol) sulfuric acid ($H_2SO_4$) and heating it at 110° C. for 5 minutes.

HPLC analysis was performed using ODS (2) C18 column (Phenomenex, USA). Water and acetonitrile gradient application time; and a component ratio are as follows: at a flow rate of 1 ml per minute for 0 minute, 68% water and 32% acetonitrile; 8 minutes, 35% water and 65% acetonitrile; 12 minutes, 0% water and 100% acetonitrile; 20 minutes, 0% water and 100% acetonitrile; 20.1 minutes, 68% water and 32% acetonitrile; and 28 minutes, 68% water and 32% acetonitrile.

Ginsenosides were detected by using a UV-detector (Younglin, Korea) at a wavelength of 203 nm.

Example 3

RNA Isolation and Real-time PCR Analysis

Total RNA was isolated from the leaf or root of 15-month-old *ginseng* using a spectrum plant total RNA kit (Sigma-Aldrich). 200 μM methyl jasmonate (MeJA) was sprayed onto the leaves of *ginseng* everyday for a total of 5 days, and samples were collected on the 6th day. The 1 μg of total RNA was used for cDNA synthesis.

Expression levels of different genes were examined by a quantitative RT-PCR using the primer sets listed in the following Table 2, and the results were normalized to the expression level of tubulin.

TABLE 2

| Gene | Sequence (5'->3') | SEQ ID NO. |
|---|---|---|
| PgDS | 5'-AAATGAAGAAGGTGGTTGGG-3' | 9 |
|  | 5'-CTCTATGCAGAGGTGTCGGA-3' | 10 |
| PgPPDS | 5'-GCCAGAGGATCCAATCAACT-3' | 11 |
|  | 5'-TCTCCATCCTTCGGGAATAA-3' | 12 |
| PgPPTS | 5'-GATGTCCTGGAATGCAGCTA-3' | 13 |
|  | 5'-AGTGCTTGACTCGTGGTGTC-3' | 14 |
| PgUGT74A1 | 5'-TATCGAACCCGAACGTACAA-3' | 15 |
|  | 5'-GTCGAGTTCCAACCACAATG-3' | 16 |
| PgUGT94B1 | 5'-GACAGAGGATTGGTTGTGGA-3' | 17 |
|  | 5'-TCAAAGGCTGATCAAGATGC-3' | 18 |
| PgTubulin | 5'-GAAGGCTTTCTTGCATTGGT-3' | 19 |
|  | 5'-CCCAGATCGTCTTCTTCTCC-3' | 20 |

Experimental Example 1

Sequence Analysis of UDP-Glycosyltransferases PgUGT74A1 and PgUGT94B1

In order to investigate the role of UDP-glycosyltransferase (UGT) involved in biosynthesis of ginsenosides, EST database analysis was first performed to clone the UGT genes from *Panax ginseng* by the method described in Example 1. Among them, two types of UGTs named as PgUGT74A1 and PgUGT94B1 were investigated to determine their roles.

The results of sequence analysis showed that they could not be specified by a sequence homology with UGTs derived from other plants including UGT from *Arabidopsis thaliana* (*A. thaliana*) (FIG. 2). To be more specific, PgUGT74A1 formed cluster with the UGT74 family of *A. thaliana*. The UGT74 family of *A. thaliana* consists of 7 types of UGTs which can be classified into 5 subfamilies (UGT74B, C, D, E1 and F). Although PgUGT74A1 formed cluster with the UGT74 family of *A. thaliana*, it could not belong to any of the 5 subfamilies, thereby indicating that PgUGT74A1 of the present invention falls into a new UGT74 subfamily distinct from other subfamilies of *A. thaliana*. Among the UGT74 families of *A. thaliana*, UGT74B1 glycosylates phenylacetothiohydroximate, which is a precursor of glucosinolate, by forming a glycosyl thioester linkage, while UGT74E2 glycosylates indole butylate by forming a glycosyl ester linkage. Likewise, UGT74F1 and UGT4F2 glycosylate salicyclate and anthranilate respectively by forming the glycosyl ester linkage as well. On the other hand, the UGT74 family members can also form an O-glycosidic linkage other than the glycosyl ester linkage. UGT74F1 is known to glycosylate salicyclate by forming a 2-O-glycosidic linkage. In addition, UGT74F1 and UGT74F2 glycosylate both salicyclate and anthranilate by forming the O-glycosidic linkage.

Therefore, even those UGTs that belong to the UGT74 family of *A. thaliana* need to be investigated to identify the type of their substrates and the linkage they form for glycosylation.

Furthermore, the analysis results demonstrated that PgUGT94B1 did not form cluster with the UGT94 family of *A. thaliana*, but instead with the UGT94 subfamilies of BpUGT94B1 (*Bellis perennis*), SiUGT94D1 (*Sesamumindicum* L.), CaUGT3 (*Catharanthus roseus*) and Cm1,2RhaT (*Citrus maxima*). Among them, BpUGT94B1 forms a β1,6 linkage to add a glucuronosyl moiety to the 3-O-glucoside of cyanidin, whereas SiUGT94D1 forms the β1,6 linkage to add glucose to the 2-O-glucoside of sesaminol. CaUGT3 forms the β1,6 linkage to transfer a glucose molecule to quercetin-3-O-glucoside, while Cm1,2RhaT forms the β1,6 linkage to add rhamnose to flavone 7-O-glucoside.

Overall, the results demonstrated that all UGT94 family members which belong to the PgUGT94B1 catalyze the glycosylation that adds the second sugar molecule to the O-glycosylated receptor regardless of the types of sugar donor and receptor.

These results indicate that PgUGT74A1 can form the O-glycosidic linkage or glycosyl ester linkage to catalyze glycosylation of ginsenosides, whereas PgUGT94B1 forms the β-glycosidic linkage to add the second sugar to the glycosylated ginsenoside, thereby catalyzing glycosylation. As indicated by the structures of ginsenosides of FIG. 1, PPD-type ginsenosides can be glycosylated at its C-3 or C-20 position, or at both positions via the O-linkage, whereas PPT-type ginsenosides can be glycosylated at its C-6 or C-20 position, or at the both positions via the O-linkage. In addition, ginsenosides having one or more sugar groups comprising ginsenoside Rb1, Compound Y and Compound O, can be further glycosylated via the β-1,6 linkage.

Based on these results of sequence analysis, the actual activities of PgUGT74A1 and PgUGT94B1 were determined through Examples as below.

Experimental Example 2

Conversion of PPD and C-K into Ginsenoside Rh2 and Ginsenoside F2 by PgUGT74A1

Based on the sequence analysis results in Experimental Example 1, substrate specificity and regioselectivity of PgUGT74A1 and PgUGT94B1 were determined as follows. First, the recombinant PgUGT of Example 1, PgUGT74A1, was incubated with 10 different types of ginsenosides (PPD, C-K, Rh2, F2, Rg3, Rd, Rg2, Rh1, F1 and PPT) in the presence of UDP-glucose, and the products converted by the recombinant PgUGT were analyzed by TLC. The results are shown in FIG. 3a.

The results showed that PgUGT74A1 did not convert ginsenosides other than PPD and C-K, indicating that PgUGT74A1 has a high acceptor specificity (FIG. 3a). The above result was confirmed by migrating spot on TLC plate. As a result, PgUGT74A1 converted PPD and C-K into ginsenoside Rh2 and ginsenoside F2 respectively.

The result was further confirmed by high performance liquid chromatography (HPLC), as shown in FIG. 3b. The results from HPLC showed that PgUGT74A1 of the present invention converted PPD and C-K into ginsenoside Rh2 and F2 respectively, as in the TLC analysis result. Unlike PgUGT74A1, PgUGT94B1 of Example 1 did not convert PPD and C-K into other ginsenosides (FIG. 3b).

As shown in the results of TLC and HPLC, PgUGT74A1 converted only the PPD-type ginsenosides such as PPD and C-K into ginsenoside Rh2 and ginsenoside F2 respectively, demonstrating its substrate specificity. Furthermore, when the carbon number that is to be glycosylated was determined, there was a specific glycosylation at the C-3 position of PPD-type ginsenoside via O-linkage while other positions such as the hydroxyl groups (—OH) at the C-12 and C-20 positions of PPD and the hydroxyl groups (—OH) at the C-3, C-6, C-12 and C-20 positions of PPT were not glycosylated, indicating that PgUGT74A1 has a regioselectivity to the C-3 position of the PPD-type ginsenosides. This result suggests that PgUGT74A1 of the present invention forms the O-glycosidic linkage to induce glycosylation.

Overall, the above results demonstrate that PgUGT74A1 specifically acts on PPD-type ginsenosides, and has a strong substrate specificity for PPD and C-K, and regioselectivity for glycosylation at the C-3 position.

Experimental Example 3

Conversion of Ginsenoside Rh2 and F2 into Ginsenoside Rg3 and Ginsenoside Rd by PgUGT94B1

It was also examined whether PgUGT94B1 cloned in Example 1 has a substrate specificity and regioselectivity like PgUGT74A1.

First, the recombinant PgUGT of Example 1, PgUGT94B1, was incubated with 10 different types of ginsenosides (PPD, C-K, Rh2, F2, Rg3, Rd, Rg2, Rh1, F1 and PPT) in the presence of UDP-glucose, and then the products converted by the recombinant PgUGT were analyzed by TLC. The results are shown in FIG. 4a.

Figure 4:
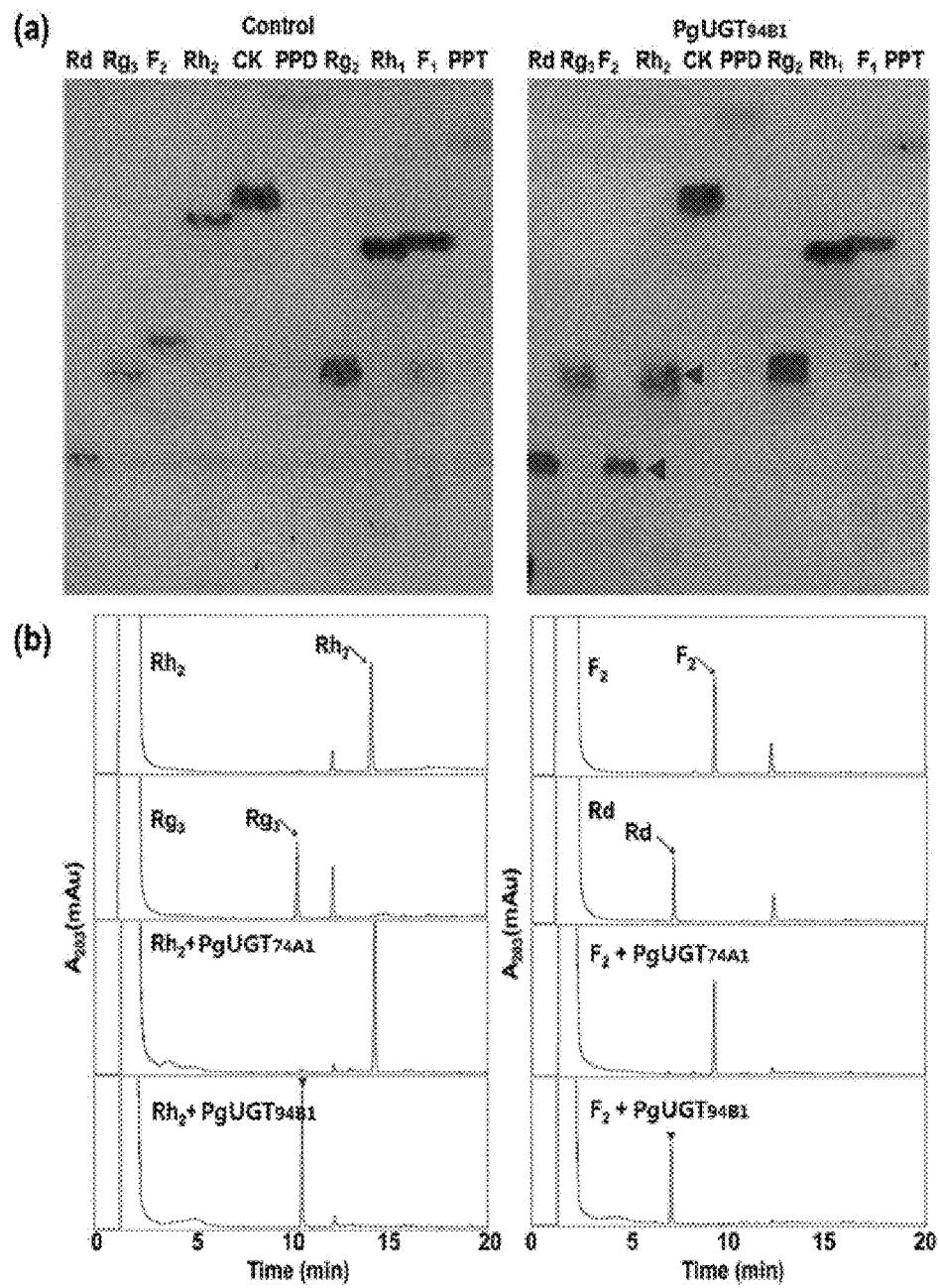
FIG. 4A-B shows the TLC and HPLC analysis results demonstrating that the UDP-glycosyltransferase, PgUGT94B1 has an activity of converting ginsenoside Rh2 and ginsenoside F2 into ginsenoside Rg3 and Rd, respectively.

As a result, PgUGT94B1 did not convert ginsenosides other than ginsenoside Rh2 and F2, indicating that PgUGT94B1 has a high acceptor specificity (FIG. 4a). This result was confirmed by a migrating spot on TLC plate. As a result, PgUGT94B1 converted ginsenoside Rh2 and ginsenoside F2 into ginsenoside Rg3 and ginsenoside Rd respectively.

The result was further confirmed by HPLC as shown in FIG. 4b. The HPLC results demonstrate that PgUGT94B1 converted ginsenoside Rh2 and F2 into ginsenoside Rg3 and Rd respectively, as in the TLC analysis result. On the other hand, PgUGT74A1 of the present invention did not convert ginsenoside Rh2 and F2, as in the results of Experimental Example 2 (FIG. 4b).

According to these results, PgUGT94B1 specifically glycosylates the O-glucoside at C-3 position of Rh2 and F2 by forming β-1,2 linkage, but not the O-glucoside at the C-20 position of C-K and F2. The above results suggest that PgUGT94B1 has a substrate specificity for Rh2 and F2 and regioselectivity for O-glucoside at the C-3 position.

Experimental Example 4

Conversion of PPD and C-K into Ginsenoside Rg3 and Rd by PgUGT74A1 and PgUGT94B1

Based on the results of Experimental Examples 2 and 3, it was conceived that when the two types of PgUGTs are used at the same time, *ginseng* PPD can be converted into ginsenoside Rh2, which in turn can be converted into Rg3, thereby producing Rg3 from PPD sequentially. Likewise, when both enzymes are used, C-K can be converted into ginsenoside F2, which in turn can be converted into ginsenoside Rd, thereby producing Rd from C-K sequentially.

In order to confirm this, the above two enzymes were reacted with PPD as a substrate in a single reaction tube. The result showed that PPD was successfully converted into Rg3 (upper panel of FIG. 5). In addition, the two enzymes were reacted with C-K as a substrate in a single reaction tube. The result showed that C-K was also successfully converted into Rd (lower panel of FIG. 5).

The above results demonstrate that PPD and C-K can be converted into Rg3 and Rd respectively by using a combination of PgUGT74A1 and PgUGT94B1 of the present invention in a single reaction tube in vitro. Thus, PgUGT74A1 and PgUGT94B1 can be used for an efficient production of Rg3 and Rd.

Experimental Example 5

Enhancement of PgUGT74A1 and PgUGT94B1 Expressions by MeJA (Methyl Jasmonate)

It was investigated whether PgUGT74A1 and PgUGT94B1 of the present invention were mainly expressed in the roots of *ginseng* that had been used for a medical purpose traditionally. Also, organ-specific expression patterns were examined for two types of PgUGTs of the present invention along with three different ginseoside biosynthetic genes such as PgDS (dammarenediol-II synthase), PgPPDS (protopanaxadiol synthase), and PgPPTS (protopanaxatriol synthase). The leaf and root of 15-month old *ginseng* were used for the expression analysis.

The result demonstrated that all of the above ginseoside biosynthetic genes were expressed in the leaf and root of *ginseng*, and particularly in the glucosylation-activated roots (FIG. 6a).

As shown in FIG. 6a, all of the 5 genes of interest were expressed in the leaf and root of *ginseng*, but there was a difference in their expression levels. The expression of PgUGT74A1 and PgUGT94B1 of the present invention was higher in the root than in the leaf. PgDS and PgPPDS genes that are involved in biosynthesis of ginsenosides showed higher expression level in the leaf of *ginseng*, whereas PgPPTS showed similar expression levels in both root and leaf of *ginseng*. These results suggest that ginsenosides are synthesized in both leaf and root of *ginseng*, but glucosylation occurs more actively in the root compared to the leaf.

Methyl jasmonate (MeJA) has been reported to enhance the expression of ginsenoside biosynthetic genes in hairy root cultures. Knowing the effect of MeJA, it was examined whether the expression of the UDP-glycosyltransferase of the present invention can be increased by MeJA.

The 15-month old *ginseng* grown in a growth chamber under LD conditions was collected, and MeJA was sprayed onto its leaves everyday for a total of 5 days. To analyze expression level of the ginsenoside biosynthetic genes, samples were collected on the 6th days. The two types of PgUGTs of the present invention showed a higher expression level in the leaves of *ginseng* which was treated with MeJA, suggesting that MeJA is capable of facilitating the expression of UGTs of the present invention (FIG. 6*b*). In addition to the above PgUGTs, MeJA also enhanced the expression of PgDS and PgPPDS. However, expression of PgPPTS was not induced by MeJA under the conditions of the present invention.

Overall, the expression analysis results demonstrate that the ginsenoside concentrations can be increased with the addition of MeJA. In this regard, the concentrations of 4 major ginsenosides were measured after spraying MeJA onto the leaf of *ginseng*. The treatment of MeJA increased the concentrations of two PPD-type ginsenosides, Rd and Rb1, by 1.55 and 1.14 times respectively (FIG. 6*c*). In addition, the treatment of MeJA increased the concentrations of two PPT-type ginsenosides, Rg1 and Re, by 2.61 and 1.45 times respectively.

These results suggest that addition of MeJA onto *ginseng* plant facilitates the expression of various ginsenoside biosynthetic genes and increases production of ginsenosides in *ginseng*. The results also suggest that since MeJA enhances the expression of PgUGT74A1 and PgUGT94B1 which are the representative glycosyltransferase of the present invention, it can be used for enhancing the expression of PgUGT74A1 and PgUGT94B1.

It will be apparent to those skilled in the art that various modifications and changes may be made without departing from the scope and spirit of the invention. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

The invention claimed is:

1. A method for preparing a glycosylated ginsenoside by converting a protopanaxadiol (PPD)-type ginsenoside, comprising reacting the PPD-type ginsenoside with an isolated Uridine diphosphate (UDP)-glycosyltransferase protein of having the sequence of SEQ ID NO:1, a transformant introduced with an expression vector comprising a polynucleotide that encodes the protein having the sequence of SEQ ID NO:1, or a culture of the transformant comprising the protein having the sequence of SEQ ID NO:1 in the presence of UDP-sugar, wherein the UDP-glycosyltransferase protein has a sugar-transfer activity to the C-3 position of PPD-type ginsenoside and wherein the PPD-type ginsenoside is PPD or Compound K (C-K).

2. The method according to claim 1, wherein the glycosylated ginsenoside is ginsenoside Rh2 or F2.

3. The method according to claim 1, which further comprises reacting the glycosylated PPD-type ginsenoside with an isolated UDP-glycosyltransferase protein having the amino acid sequence of SEQ ID NO: 3, a transformant introduced with a vector comprising a polynucleotide that encodes the protein having the sequence of SEQ ID NO:3, or a culture of the transformant comprising the protein having the sequence of SEQ ID NO:3.

4. The method according to claim 3, which comprises conversion of ginsenoside Rh2 into ginsenoside Rg3 or conversion of ginsenoside F2 into ginsenoside Rd by the isolated UDP-glycosyltransferase protein which is represented by the amino acid sequence of SEQ ID NO: 3.

* * * * *

SEQUENCE LISTING

<160> NUMBER OF SEQ ID NOS: 20

<210> SEQ ID NO 1
<211> LENGTH: 451
<212> TYPE: PRT
<213> ORGANISM: Panax ginseng

<400> SEQUENCE: 1

```
Met Leu Ser Lys Thr His Ile Met Phe Ile Pro Phe Pro Ala Gln Gly
1               5                   10                  15

His Met Ser Pro Met Met Gln Phe Ala Lys Arg Leu Ala Trp Lys Gly
            20                  25                  30

Val Arg Ile Thr Ile Val Leu Pro Ala Gln Ile Arg Asp Ser Met Gln
        35                  40                  45

Ile Thr Asn Ser Leu Ile Asn Thr Glu Cys Ile Ser Phe Asp Phe Asp
    50                  55                  60

Lys Asp Asp Gly Met Pro Tyr Ser Met Gln Ala Tyr Met Gly Val Val
65                  70                  75                  80

Lys Leu Lys Val Thr Asn Lys Leu Ser Asp Leu Leu Glu Lys Gln Lys
                85                  90                  95

Thr Asn Gly Tyr Pro Val Asn Leu Leu Val Val Asp Ser Leu Tyr Pro
            100                 105                 110

Ser Arg Val Glu Met Cys His Gln Leu Gly Val Lys Gly Ala Pro Phe
        115                 120                 125

Phe Thr His Ser Cys Ala Val Gly Ala Ile Tyr Tyr Asn Ala His Leu
    130                 135                 140

Gly Lys Leu Lys Ile Pro Pro Glu Glu Gly Leu Thr Ser Val Ser Leu
145                 150                 155                 160

Pro Ser Ile Pro Leu Leu Gly Arg Asp Asp Leu Pro Ile Ile Arg Thr
                165                 170                 175

Gly Thr Phe Pro Asp Leu Phe Glu His Leu Gly Asn Gln Phe Ser Asp
            180                 185                 190

Leu Asp Lys Ala Asp Trp Ile Phe Phe Asn Thr Phe Asp Lys Leu Glu
        195                 200                 205

Asn Glu Glu Ala Lys Trp Leu Ser Ser Gln Trp Pro Ile Thr Ser Ile
    210                 215                 220

Gly Pro Leu Ile Pro Ser Met Tyr Leu Asp Lys Gln Leu Pro Asn Asp
```

```
                225                 230                 235                 240
Lys Gly Asn Gly Ile Asn Leu Tyr Lys Ala Asp Val Gly Ser Cys Ile
                245                 250                 255

Lys Trp Leu Asp Ala Lys Asp Pro Gly Ser Val Val Tyr Ala Ser Phe
            260                 265                 270

Gly Ser Val Lys His Asn Phe Gly Asp Asp Tyr Met Asp Glu Val Ala
            275                 280                 285

Trp Gly Leu Leu His Ser Lys Tyr Asn Phe Ile Trp Val Val Ile Glu
            290                 295                 300

Pro Glu Arg Thr Lys Leu Ser Ser Asp Phe Leu Ala Glu Ala Glu Glu
305                 310                 315                 320

Lys Gly Leu Ile Val Ser Trp Cys Pro Gln Leu Glu Val Leu Ser His
                325                 330                 335

Lys Ser Ile Gly Ser Phe Met Thr His Cys Gly Trp Asn Ser Thr Val
                340                 345                 350

Glu Ala Leu Ser Leu Gly Val Pro Met Val Ala Val Pro Gln Gln Phe
            355                 360                 365

Asp Gln Pro Val Asn Ala Lys Tyr Ile Val Asp Val Trp Gln Ile Gly
            370                 375                 380

Val Arg Val Pro Ile Gly Glu Asp Gly Val Val Leu Arg Gly Glu Val
385                 390                 395                 400

Ala Asn Cys Ile Lys Asp Val Met Glu Gly Glu Ile Gly Asp Glu Leu
                405                 410                 415

Arg Gly Asn Ala Leu Lys Trp Lys Gly Leu Ala Val Glu Ala Met Glu
            420                 425                 430

Lys Gly Gly Ser Ser Asp Lys Asn Ile Asp Glu Phe Ile Ser Lys Leu
            435                 440                 445

Val Ser Ser
    450

<210> SEQ ID NO 2
<211> LENGTH: 1356
<212> TYPE: DNA
<213> ORGANISM: Panax ginseng

<400> SEQUENCE: 2
atgctgagca aaactcacat tatgttcatc ccattcccag ctcaaggcca catgagccca      60
atgatgcaat cgccaagcg tttagcctgg aaaggcgtgc gaatcacgat agttcttcct     120
gctcaaattc gagattccat gcaaataacc aactcattga tcaacactga gtgcatctcc     180
tttgattttg ataaagatga tgggatgcca tacagcatgc aggcttatat gggagttgta     240
aaactcaaag tcacaaataa actgagtgac ctactcgaga agcaaaaaac aaatggctac     300
cctgttaatt tgctggtggt tgattcatta tatccatctc gggtagaaat gtgccaccaa     360
cttggggtaa aaggagctcc atttttcact cactcttgtg ctgttggtgc catttattat     420
aatgctcact tagggaaatt gaagatacct cctgaggaag gcttgacttc tgtttcattg     480
ccttcaattc cattgttggg gagagatgat tgccaattat tcggactgg caccttcct     540 gatctctttg agcatttggg gaatcagttt tcagatcttg ataaagcgga ttggatcttt     600
ttcaatactt ttgataagct tgaaaatgag gaagcaaaat ggctatctag ccaatggcca     660
attacatcca tcggaccatt aatcccttca atgtacttag acaaacaatt accaaatgac     720
aaaggcaatg gcattaattt gtacaaggca gacgtcggat cgtgcatcaa gtggctagac     780
gccaaagacc ctggctcggt agtctacgcc tcattcggga gcgtgaagca caacttcggc     840
```

```
gatgactaca tggacgaagt agcatggggc ttgttacata gcaaataaa cttcatatgg    900 gttgttatcg aacccgaacg tacaaagctc tctagcgatt tcttggcaga ggcagaggaa    960
aaaggcctaa tagtgagttg gtgccctcaa ctcgaagttt tgtcacataa atctataggg   1020
agttttatga ctcattgtgg ttggaactcg acggttgagg cattgagttt gggcgtgcca   1080
atggtggcag tgccacaaca gtttgatcag cctgttaatg ctaagtatat cgtggacgta   1140
tggcaaattg gggttcgggt tccgattggt gaagatgggg ttgttttgag gggagaagtt   1200
gctaactgta taaggatgt tatggagggg gaaatagggg atgagcttag agggaatgct   1260
ttgaaatgga aggggttggc tgtggaggca atggagaaag ggggtagctc tgataagaat   1320
attgatgagt tcatttcaaa gcttgtgtcc tcctga                             1356
```

<210> SEQ ID NO 3
<211> LENGTH: 442
<212> TYPE: PRT
<213> ORGANISM: Panax ginseng

<400> SEQUENCE: 3

```
Met Asp Asn Gln Asn Gly Arg Ile Ser Ile Ala Leu Leu Pro Phe Leu
1               5                   10                  15

Ala His Gly His Ile Ser Pro Phe Phe Glu Leu Ala Lys Gln Leu Ala
            20                  25                  30

Lys Arg Asn Cys Asn Val Phe Leu Cys Ser Thr Pro Ile Asn Leu Ser
        35                  40                  45

Ser Ile Lys Asp Lys Asp Ser Ser Ala Ser Ile Lys Leu Val Glu Leu
    50                  55                  60

His Leu Pro Ser Ser Pro Asp Leu Pro Pro His Tyr His Thr Thr Asn
65                  70                  75                  80

Gly Leu Pro Ser His Leu Met Leu Pro Leu Arg Asn Ala Phe Glu Thr
                85                  90                  95

Ala Gly Pro Thr Phe Ser Glu Ile Leu Lys Thr Leu Asn Pro Asp Leu
            100                 105                 110

Leu Ile Tyr Asp Phe Asn Pro Ser Trp Ala Pro Glu Ile Ala Ser Ser
        115                 120                 125

His Asn Ile Pro Ala Val Tyr Phe Leu Thr Thr Ala Ala Ser Ser
    130                 135                 140

Ser Ile Gly Leu His Ala Phe Lys Asn Pro Gly Glu Lys Tyr Pro Phe
145                 150                 155                 160

Pro Asp Phe Tyr Asp Asn Ser Asn Ile Thr Pro Glu Pro Pro Ser Ala
                165                 170                 175

Asp Asn Met Lys Leu Leu His Asp Phe Ile Ala Cys Phe Glu Arg Ser
            180                 185                 190

Cys Asp Ile Ile Leu Ile Lys Ser Phe Arg Glu Leu Glu Gly Lys Tyr
        195                 200                 205

Ile Asp Leu Leu Ser Thr Leu Ser Asp Lys Thr Leu Val Pro Val Gly
    210                 215                 220

Pro Leu Val Gln Asp Pro Met Gly His Asn Glu Asp Pro Lys Thr Glu
225                 230                 235                 240

Gln Ile Ile Asn Trp Leu Asp Lys Arg Ala Glu Ser Thr Val Val Phe
                245                 250                 255

Val Cys Phe Gly Ser Glu Tyr Phe Leu Ser Asn Glu Glu Leu Glu Glu
            260                 265                 270

Val Ala Ile Gly Leu Glu Ile Ser Thr Val Asn Phe Ile Trp Ala Val
```

```
            275                 280                 285
Arg Leu Ile Glu Gly Glu Lys Lys Gly Ile Leu Pro Glu Gly Phe Val
            290                 295                 300
Gln Arg Val Gly Asp Arg Gly Leu Val Val Glu Gly Trp Ala Pro Gln
305                 310                 315                 320
Ala Arg Ile Leu Gly His Ser Ser Thr Gly Phe Val Ser His Cys
            325                 330                 335
Gly Trp Ser Ser Ile Ala Glu Ser Met Lys Phe Gly Val Pro Val Ile
            340                 345                 350
Ala Met Ala Arg His Leu Asp Gln Pro Leu Asn Gly Lys Leu Ala Ala
            355                 360                 365
Glu Val Gly Val Gly Met Glu Val Val Arg Asp Glu Asn Gly Lys Tyr
            370                 375                 380
Lys Arg Glu Gly Ile Ala Glu Val Ile Arg Lys Val Val Glu Lys
385                 390                 395                 400
Ser Gly Glu Val Ile Arg Arg Lys Ala Arg Glu Leu Ser Glu Lys Met
            405                 410                 415
Lys Glu Lys Gly Glu Gln Ile Asp Arg Ala Leu Glu Glu Leu Val
            420                 425                 430
Gln Ile Cys Lys Lys Lys Lys Asp Glu Gln
            435                 440

<210> SEQ ID NO 4
<211> LENGTH: 1329
<212> TYPE: DNA
<213> ORGANISM: Panax ginseng

<400> SEQUENCE: 4
atggataacc aaaatggtag aatcagtata gcgttgctac catttttagc ccatggtcac      60
atatctccct tctttgagct agccaaacaa ctcgcgaaaa gaaattgcaa tgttttcctc     120
tgttctaccc caatcaatct tagctccatc aaggataagg attcctctgc ttctataaaa     180
ctagttgagc ttcatcttcc atcttcccct gatcttcctc ctcactatca caccacaaat     240
ggcctccctt cccatctcat gctcccactc agaaacgcct tgaaactgc aggcccccacc     300
ttctctgaaa tccttaaaac cttaaaccc gatttgctta tttatgattt caatccctca     360
tgggcaccgg agatcgcttc gtctcacaat attccggcag tttatttcct aaccacggca     420
gcagccagct cttccattgg cctacatgct ttcaaaaacc caggtgaaaa atacccattt     480
ccagattttt atgataacag taatattacc cctgaaccac ttctgcaga taacatgaag     540
ctacttcatg attttatcgc ttgtttcgaa cgatcttgcg acattatttt gattaagagt     600
tttagagaac tagaagggaa atatattgat ttgctttcca ctttatctga taaaactttg     660
gttcctgttg gtccactcgt tcaagatcct atgggccata tgaagatcc aaaaacagag     720
cagattataa actggcttga caaaggggct gaatctacag tggtgttttgt ctgctttgga     780
agtgagtatt ttctctccaa tgaggaattg aagaagtag caattgggct agagattagc     840
acggttaatt tcatatgggc tgtgagatta attgaaggag agaaaaaagg gatttttacca     900
gaggggtttg ttcaaagggt aggagacaga ggattggttg tggaggggtg ggctccacag     960
gcaagaattt taggacattc aagcaccggt gggtttgtga gccattgtgg gtggagttct    1020
attgcggaga gtatgaagtt tggggttcca gtaattgcca tggccaggca tcttgatcag    1080
cctttgaatg gtaagctggc ggcgaggtt ggtgtgggca tggaggttgt gagagatgag    1140
aatgggaagt ataagagaga agggattgca gaggtaataa gaaaagtggt tgtggagaaa    1200
```

```
agtggggagg ttatcaggag gaaagcaagg gagttgagtg agaaaatgaa agagaaagga    1260
gagcaagaga ttgatagggc attggaggag ctagtacaaa tttgtaagaa gaagaaagat    1320
gaacaatag                                                            1329
```

<210> SEQ ID NO 5
<211> LENGTH: 39
<212> TYPE: DNA
<213> ORGANISM: Artificial Sequence
<220> FEATURE:
<223> OTHER INFORMATION: primer PgUGT74A1-BamHI

<400> SEQUENCE: 5

```
aggcatggat ccctgagcaa aactcacatt atgttcatc                             39
```

<210> SEQ ID NO 6
<211> LENGTH: 42
<212> TYPE: DNA
<213> ORGANISM: Artificial Sequence
<220> FEATURE:
<223> OTHER INFORMATION: primer PgUGT74A1-EcoRI

<400> SEQUENCE: 6

```
aggcatgaat tctcaggagg acacaagctt tgaaatgaac tc                         42
```

<210> SEQ ID NO 7
<211> LENGTH: 39
<212> TYPE: DNA
<213> ORGANISM: Artificial Sequence
<220> FEATURE:
<223> OTHER INFORMATION: primer PgUGT94B1-BamHI

<400> SEQUENCE: 7

```
aggcatggat ccgataacca aaaggtaga atcagtata                              39
```

<210> SEQ ID NO 8
<211> LENGTH: 42
<212> TYPE: DNA
<213> ORGANISM: Artificial Sequence
<220> FEATURE:
<223> OTHER INFORMATION: primer PgUGT94B1-EcoR

<400> SEQUENCE: 8

```
aggcatgaat tcctattgtt catctttctt cttcttacaa at                         42
```

<210> SEQ ID NO 9
<211> LENGTH: 20
<212> TYPE: DNA
<213> ORGANISM: Artificial Sequence
<220> FEATURE:
<223> OTHER INFORMATION: primer for PgDS

<400> SEQUENCE: 9

```
aaatgaagaa ggtggttggg                                                  20
```

<210> SEQ ID NO 10
<211> LENGTH: 20
<212> TYPE: DNA
<213> ORGANISM: Artificial Sequence
<220> FEATURE:
<223> OTHER INFORMATION: primer for PgDS

<400> SEQUENCE: 10

```
ctctatgcag aggtgtcgga                                                  20
```

```
<210> SEQ ID NO 11
<211> LENGTH: 20
<212> TYPE: DNA
<213> ORGANISM: Artificial Sequence
<220> FEATURE:
<223> OTHER INFORMATION: primer for PgPPDS

<400> SEQUENCE: 11
gccagaggat ccaatcaact                                                 20

<210> SEQ ID NO 12
<211> LENGTH: 20
<212> TYPE: DNA
<213> ORGANISM: Artificial Sequence
<220> FEATURE:
<223> OTHER INFORMATION: primer for PgPPDS

<400> SEQUENCE: 12
tctccatcct tcgggaataa                                                 20

<210> SEQ ID NO 13
<211> LENGTH: 20
<212> TYPE: DNA
<213> ORGANISM: Artificial Sequence
<220> FEATURE:
<223> OTHER INFORMATION: primer for PgPPTS

<400> SEQUENCE: 13
gatgtcctgg aatgcagcta                                                 20

<210> SEQ ID NO 14
<211> LENGTH: 20
<212> TYPE: DNA
<213> ORGANISM: Artificial Sequence
<220> FEATURE:
<223> OTHER INFORMATION: primer for PgPPTS

<400> SEQUENCE: 14
agtgcttgac tcgtggtgtc                                                 20

<210> SEQ ID NO 15
<211> LENGTH: 20
<212> TYPE: DNA
<213> ORGANISM: Artificial Sequence
<220> FEATURE:
<223> OTHER INFORMATION: primer for PgUGT74A1

<400> SEQUENCE: 15
tatcgaaccc gaacgtacaa                                                 20

<210> SEQ ID NO 16
<211> LENGTH: 20
<212> TYPE: DNA
<213> ORGANISM: Artificial Sequence
<220> FEATURE:
<223> OTHER INFORMATION: primer for PgUGT74A1

<400> SEQUENCE: 16
gtcgagttcc aaccacaatg                                                 20

<210> SEQ ID NO 17
<211> LENGTH: 20
<212> TYPE: DNA
<213> ORGANISM: Artificial Sequence
<220> FEATURE:
<223> OTHER INFORMATION: primer for PgUGT94B1
```

```
<400> SEQUENCE: 17
gacagaggat tggttgtgga                                              20

<210> SEQ ID NO 18
<211> LENGTH: 20
<212> TYPE: DNA
<213> ORGANISM: Artificial Sequence
<220> FEATURE:
<223> OTHER INFORMATION: primer for PgUGT94B1

<400> SEQUENCE: 18
tcaaaggctg atcaagatgc                                              20

<210> SEQ ID NO 19
<211> LENGTH: 20
<212> TYPE: DNA
<213> ORGANISM: Artificial Sequence
<220> FEATURE:
<223> OTHER INFORMATION: primer for PgTubulin

<400> SEQUENCE: 19
gaaggctttc ttgcattggt                                              20

<210> SEQ ID NO 20
<211> LENGTH: 20
<212> TYPE: DNA
<213> ORGANISM: Artificial Sequence
<220> FEATURE:
<223> OTHER INFORMATION: primer for PgTubulin

<400> SEQUENCE: 20
cccagatcgt cttcttctcc                                              20
```